(12) United States Patent
Bui et al.

(10) Patent No.: US 10,272,027 B2
(45) Date of Patent: *Apr. 30, 2019

(54) LIPSTICK COMPOSITION HAVING IMPROVED COMFORT

(71) Applicant: L'OREAL, Paris (FR)

(72) Inventors: Hy Si Bui, Piscataway, NJ (US); Rita Jaky El-Khouri, Morristown, NJ (US); Mita Trivedi, Colonia, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,851

(22) Filed: Jun. 18, 2014

(65) Prior Publication Data

US 2015/0366780 A1  Dec. 24, 2015

(51) Int. Cl.
| | |
|---|---|
| *A61Q 1/06* | (2006.01) |
| *A61K 8/895* | (2006.01) |
| *A61K 8/89* | (2006.01) |
| *A61K 8/81* | (2006.01) |
| *A61K 8/92* | (2006.01) |
| *A61K 8/41* | (2006.01) |
| *A61K 8/31* | (2006.01) |
| *A61K 8/58* | (2006.01) |
| *A61Q 19/06* | (2006.01) |
| *A61K 8/891* | (2006.01) |
| *A61K 8/02* | (2006.01) |

(52) U.S. Cl.
CPC ............ *A61K 8/895* (2013.01); *A61K 8/0229* (2013.01); *A61K 8/31* (2013.01); *A61K 8/416* (2013.01); *A61K 8/585* (2013.01); *A61K 8/8117* (2013.01); *A61K 8/89* (2013.01); *A61K 8/891* (2013.01); *A61K 8/92* (2013.01); *A61Q 1/06* (2013.01); *A61Q 19/06* (2013.01)

(58) Field of Classification Search
None
See application file for complete search history.

(56) References Cited

U.S. PATENT DOCUMENTS

| | | | |
|---|---|---|---|
| 4,693,935 A | 9/1987 | Mazurek | |
| 4,972,037 A | 11/1990 | Garbe et al. | |
| 4,981,902 A | 1/1991 | Mitra et al. | |
| 4,981,903 A | 1/1991 | Garbe et al. | |
| 5,061,481 A | 10/1991 | Suzuki et al. | |
| 5,209,924 A | 5/1993 | Garbe et al. | |
| 5,219,560 A | 6/1993 | Suzuki et al. | |
| 5,262,087 A | 11/1993 | Tachibana et al. | |
| 5,468,477 A | 11/1995 | Kumar et al. | |
| 5,849,275 A | 12/1998 | Calello et al. | |
| 5,919,879 A | 7/1999 | Midha et al. | |
| 6,033,650 A | 3/2000 | Calello et al. | |
| 6,143,283 A * | 11/2000 | Calello et al. | 424/64 |
| 6,338,839 B1 | 1/2002 | Auguste et al. | |
| 6,555,117 B2 | 4/2003 | Midha et al. | |
| 6,908,621 B2 | 6/2005 | Jose et al. | |
| 7,879,316 B2 | 2/2011 | Ferrari et al. | |
| 8,586,013 B2 | 11/2013 | Bradshaw et al. | |
| 8,603,444 B2 | 12/2013 | Bui | |
| 2002/0004054 A1 | 1/2002 | Calello et al. | |
| 2003/0235552 A1 | 12/2003 | Yu | |
| 2004/0126350 A1 | 7/2004 | Blin et al. | |
| 2004/0156806 A1 | 8/2004 | Patil et al. | |
| 2005/0089498 A1 | 4/2005 | Patil et al. | |
| 2006/0292096 A1 | 12/2006 | Yu | |
| 2007/0093619 A1 | 4/2007 | Bui et al. | |
| 2011/0293550 A1 | 12/2011 | Bui et al. | |
| 2012/0171137 A1 | 7/2012 | Bradshaw et al. | |
| 2012/0219516 A1* | 8/2012 | Ramada | A61Q 1/06 424/64 |
| 2012/0288462 A1* | 11/2012 | Lebok | A61K 8/0229 424/64 |
| 2012/0301415 A1 | 11/2012 | Bui et al. | |
| 2013/0171084 A1 | 7/2013 | Kawaratani et al. | |
| 2013/0224130 A1 | 8/2013 | Bui et al. | |

FOREIGN PATENT DOCUMENTS

| | | |
|---|---|---|
| WO | 93/23446 A2 | 11/1993 |
| WO | 95/06078 A1 | 3/1995 |
| WO | 01/32727 A1 | 5/2001 |
| WO | 01/32737 A1 | 5/2001 |

OTHER PUBLICATIONS

U.S. Appl. No. 14/307,815, filed Jun. 18, 2014, Hy Si Bui.
U.S. Appl. No. 14/307,831, filed Jun. 18, 2014, Hy Si Bui.

* cited by examiner

*Primary Examiner* — Jyothsna A Venkat
(74) *Attorney, Agent, or Firm* — Oblon, McClelland, Maier & Neustadt, L.L.P.

(57) ABSTRACT

Provided are cosmetic compositions comprising a silicone acrylate copolymer, a polypropylsilsesquioxane film forming resin, a hydrocarbon-based resin, a non-volatile oil, a volatile hydrocarbon solvent, and optionally a wax, wherein the ratio of the silicone acrylate copolymer to the polypropylsilsesquioxane resin is from about 1:1 to about 4:1, the weight percent ratio of silicone acrylate copolymer plus the polypropylsilsesquioxane film forming resin to the at least one hydrocarbon-based resin is from about 1.5:1 to about 30:1 on a dry weight basis, and the total amount of the polypropyl silsesquioxane film forming resin and the silicone acrylate copolymer is greater than about 10% on a dry weight basis relative to the weight of the composition.

8 Claims, No Drawings

US 10,272,027 B2

LIPSTICK COMPOSITION HAVING IMPROVED COMFORT

BACKGROUND OF THE INVENTION

The present invention relates to a lipstick composition comprising a silicone acrylate copolymer, a polypropylsilsesquioxane film forming resin, a hydrocarbon-based resin, a wax, a non-volatile oil, and a volatile hydrocarbon solvent, wherein the ratio of the silicone acrylate copolymer to the polypropylsilsesquioxane resin is from about 1:1 to about 4:1, the total amount of the polypropylsilsesquioxane film forming resin and the silicone acrylate copolymer resin being equal to or greater than 10% of the composition, on a dry weight basis. The lipstick can be in solid or liquid form, preferably solid.

Currently, commercially available long wear lipsticks are typically comprised of a silicone resin, such as MQ resin, and a plasticizing agent. MQ resin-containing lipsticks are disclosed, for example, in U.S. Pat. No. 6,908,621. These products tend to have tacky feel.

The use of some silicone polymers in cosmetics, can improve comfort by providing an overall smooth feel. For example, polyorganosiloxane-containing polymers in cosmetic compositions, including lipsticks, are discussed in U.S. Pat. No. 7,879,316. The use of silicone acrylate copolymers and polypropylsilsesquioxane resins in liquid lipstick compositions has been described, for example, in US2007/0093619 and US2012/0301415. Typically, non-volatile oils are used in these compositions to provide shine. However, the incorporation of these non-volatile oils often reduces (compromises) wear properties.

Surprisingly, applicants have found that combining at least one polypropylsilsesquioxane film forming resin with at least one silicone acrylate copolymer and a hydrocarbon-based resin in a particular ratio, together with a wax, a non-volatile oil, and a volatile hydrocarbon solvent, affords a long wear lipstick composition that is more comfortable (e.g., less tacky) than MQ-based lip compositions.

BRIEF SUMMARY OF THE INVENTION

The present invention relates to a cosmetic composition comprising:
 (a) from about 2% to about 40% by weight of at least one silicone acrylate copolymer;
 (b) from about 2% to about 40% by weight of at least one polypropylsilsesquioxane film forming resin;
 (c) from about 0.5% to about 7.5% of at least one hydrocarbon-based resin
 (d) from about 10% to about 60% by weight of at least one volatile hydrocarbon solvent;
 (e) from about 5% to about 60% of at least one non-volatile oil;
 (f) optionally at least one wax; and
 (g) optionally at least one colorant;
 wherein the weight percent ratio of the silicone acrylate copolymer (a) to the at least one polypropylsilsesquioxane film forming resin (b) is from about 1:1 to about 4:1 on a dry weight basis; the weight percent ratio of silicone acrylate copolymer (a) plus the at least one polypropylsilsesquioxane film forming resin (b) to the at least one hydrocarbon-based resin (c) is from about 1.5:1 to about 30:1 on a dry weight basis; the total weight percent of the at least one silicone acrylate copolymer (a) plus the at least one polypropylsilsesquioxane film forming resin (b) is greater than about 10% on a dry weight basis; each weight being relative to the total weight of the composition.

The invention also relates to a method for making up the lips by applying to the lips the above composition.

The invention also relates to a method for making up the lips comprising (a) providing the above-described composition, and (b) instructions on applying said composition to the lips.

DETAILED DESCRIPTION OF THE INVENTION

It has been unexpectedly discovered that a cosmetic composition containing at least one silicone acrylate copolymer and at least one polypropylsilsesquioxane film forming resin in a weight percent ratio of from about 1:1 to about 4:1, together with at least one hydrocarbon-based resin, at least one wax, at least one non-volatile oil and at least one volatile hydrocarbon solvent provides a lipstick composition with improved comfort (less tackiness).

"About" as used herein means within 10% of the indicated number (e.g. "about 10%" means 9%-11% and "about 2%" means 1.8%-2.2%).

"Additional non-volatile solvents/oil" means non-volatile solvent/oil other than that which may be associated with other components in the formula.

"At least one" means one or more and thus includes individual components as well as mixture/combinations.

"Comprising" it is meant that other steps and/or ingredients which do not affect the end result may be added. The products, compositions, methods and processes of the present invention can include all the essential elements and limitations of the invention described herein as well as any of the additional or optional ingredients, components, steps, or limitations described herein.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the conditioning compositions of the invention. Thus, for example, "free of non-volatile solvents" means that non-volatile solvents are preferably omitted (that is 0% by weight), but can be present in the composition at an amount of less than about 0.25% by weight, typically less than about 0.1% by weight, typically less than about 0.05% by weight, based on the total weight of the composition as a whole.

The term "film forming polymer" means that the polymer is capable of forming a film, in particular a substantive film, on the lips, for example, after a solvent accompanying the film former has evaporated, absorbed into and/or dissipated on the lips. In the context of this invention, the silicone acrylate copolymer is a film forming polymer.

By the term "polypropylsilsesquioxane film-forming resin" it is meant a polymer that is amorphous and has a low Tg of from about 0° C. to about 5° C. and has substantive, film forming properties when applied to a keratinous material such as the lips.

The term "film forming hydrocarbon-based resin" means a carbon-based polymer that is amorphous and has a Tg greater than about 20° C. In the context of this invention, the hydrocarbon-based resin is a film forming hydrocarbon-based resin.

The term "glass transition temperature" (Tg) generally refers to the temperature at which amorphous material changes from a glassy solid state to a rubbery state. The temperature may be measured by standard techniques in the art, such a Differential Scanning calorimetry (DSM), e.g., according to a standard protocol such as ASTM D3418-97 standard. The Tg of the film, such as those formed by incorporating (a) and (b) in the lipstick formulas of the invention, can be measured, for example by drawing down the composition on a glass plate using a draw dawn bar until the thickness of the resulting film is about 6 mil. The films are allowed to dry, peeled from the plate and then subjected to Differential Scanning calorimetry (DSC) scanning.

"Gloss" refers to the overall shine of a product once applied to a keratinous substrate, such as the lips. It is measured using a gloss meter and the units of measurement are gloss units (GU).

"INCI" is an abbreviation of International Nomenclature of Cosmetic Ingredients, which is a system of names provided by the International Nomenclature Committee of the Personal Care Products Council to describe personal care ingredients.

"Substituted" as used herein, means comprising at least one substituent. Non-limiting examples of substituents include atoms, such as oxygen atoms and nitrogen atoms, non-functional groups such as alkyl groups, as well as functional groups such as amine groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Tackiness" as used herein refers to the adhesion between two substances. For example, the more tackiness there is between two substances, the more adhesion there is between the substances. To quantify "tackiness," it is useful to determine the "work of adhesion" as defined by IUPAC associated with the two substances. Generally speaking, the work of adhesion measures the amount of work necessary to separate two substances. Thus, the greater the work of adhesion associated with two substances, the greater the adhesion there is between the substances, meaning the greater the tackiness is between the two substances.

Work of adhesion and, thus, tackiness, can be quantified using acceptable techniques and methods generally used to measure adhesion, and is typically reported in units of force time (for example, gram seconds ("g s")). For example, the TA-XT2 from Stable Micro Systems, Ltd. can be used to determine adhesion following the procedures set forth in the TA-XT2 Application Study (ref: MATI/PO.25), revised January 2000, the entire contents of which are hereby incorporated by reference. According to this method, desirable values for work of adhesion for substantially non-tacky substances include less than about 0.5 g s, less than about 0.4 g s, less than about 0.3 g s and less than about 0.2 g s. As known in the art, other similar methods can be used on other similar analytical devices to determine adhesion.

The "wear" of compositions as used herein, refers to the extent by which the color of the composition remains the same or substantially the same as at the time of application, as viewed by the naked eye, after a certain period or an extended period of time. Wear properties may be evaluated by any method known in the art for evaluating such properties. For example, wear may be evaluated by a test involving the application of a composition to human hair, skin or lips and evaluating the color of the composition after a specified period of time. For example, the color of a composition may be evaluated immediately following application to skin or lips and these characteristics may then be re-evaluated and compared after a certain amount of time. Further, these characteristics may be evaluated with respect to other compositions, such as commercially available compositions. For lip compositions, "long wear" typically means the composition remains on the lips at least about 4 hours up to about 24 hours, and retains rich color even after eating.

All percentages, parts and ratios are based upon the total weight of the compositions of the present invention unless otherwise indicated.

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

As used herein a range of ratios is meant to include every specific ratio within, and combination of subranges between, the given ranges.

According to various embodiments of the disclosure, the ratio of the weight percent of the at least one silicone acrylate copolymer (a) to the weight percent of the at least one polypropylsilsesquioxane film forming resin (b) is from about 1:1 to about 4:1, such as from about 1:1 to about 3:1, and from about 1:1 to about 2:1, and from about 1:1 to about 1.8:1.

In a particular embodiment the ratio of (a) to (b) is from about 1:1 to about 4:1.

In various embodiments, the weight percent ratio of (a) to (b) is about 1:1, or about 1.04:1.

In an embodiment the present invention relates to a cosmetic composition comprising:
  (a) from about 2% to about 40% by weight of at least one silicone acrylate copolymer;
  (b) from about 2% to about 40% by weight of at least one polypropylsilsesquioxane film forming resin;
  (c) from about 0.5% to about 7.5% of at least one hydrocarbon-based resin;
  (d) from about 10% to about 60% by weight of at least one volatile hydrocarbon solvent;
  (e) from about 5% to about 60% of at least one non-volatile oil;
  (f) optionally at least one wax; and
  (g) optionally at least one colorant;
  wherein the weight percent ratio of the silicone acrylate copolymer (a) to the at least one polypropylsilsesquioxane film forming resin (b) is from about 1:1 to about 4:1 on a dry weight basis; the weight percent ratio of silicone acrylate copolymer (a) plus the at least one polypropylsilsesquioxane film forming resin (b) to the at least one hydrocarbon-based resin (c) is from about 1.5:1 to about 30:1 on a dry weight basis; the total weight percent of the at least one silicone acrylate copolymer (a) plus the at least one polypropylsilsesquioxane film forming resin (b) is greater than about 10% on a dry weight basis; each weight being relative to the total weight of the composition.

In an embodiment the present invention relates to a liquid cosmetic composition comprising:
  (a) from about 5% to about 25% by weight of at least one silicone acrylate copolymer;
  (b) from about 5% to about 22% by weight of at least one polypropylsilsesquioxane film forming resin;
  (c) from about 0.5% to about 7.5% of at least one hydrocarbon-based resin;
  (d) from about 10% to about 60% by weight of at least one volatile hydrocarbon solvent;
  (e) from about 10% to about 50% of at least one non-volatile oil;

(f) about 0% wax; and
(g) optionally at least one colorant;
wherein the weight percent ratio of the silicone acrylate copolymer (a) to the at least one polypropylsilsesquioxane film forming resin (b) is from about 1:1 to about 2:1 on a dry weight basis; the weight percent ratio of silicone acrylate copolymer (a) plus the at least one polypropylsilsesquioxane film forming resin (b) to the at least one hydrocarbon-based resin (c) is from about 1.9:1 to about 24:1 on a dry weight basis; the total weight percent of the at least one silicone acrylate copolymer (a) plus the at least one polypropylsilsesquioxane film forming resin (b) is greater than about 10% on a dry weight basis; each weight being relative to the total weight of the composition.

In another embodiment the invention relates to a solid cosmetic composition comprising:
(a) from about 5% to about 25% by weight of at least one silicone acrylate copolymer;
(b) from about 5% to about 22% by weight of at least one polypropylsilsesquioxane film forming resin;
(c) from about 1% to about 4% of at least one hydrocarbon-based resin (d) from about 10% to about 60% by weight of at least one volatile hydrocarbon solvent;
(e) from about 10% to about 50% of at least one non-volatile oil;
(f) from about 5% to about 15% of at least one wax; and
(g) optionally at least one colorant;
wherein the weight percent ratio of the silicone acrylate copolymer (a) to the at least one polypropylsilsesquioxane film forming resin (b) is from about 1:1 to about 4:1 on a dry weight basis; the weight percent ratio of silicone acrylate copolymer (a) plus the at least one polypropylsilsesquioxane film forming resin (b) to the at least one hydrocarbon-based resin (c) is from about 4.5:1 to about 6.5:1 on a dry weight basis; the total weight percent of the at least one silicone acrylate copolymer (a) plus the at least one polypropylsilsesquioxane film forming resin (b) is greater than about 11% on a dry weight basis; each weight being relative to the total weight of the composition.

In another embodiment the invention relates to a method of improving the comfort of a lipstick composition comprising including in said composition:
(a) from about 2% to about 40% by weight of at least one silicone acrylate copolymer;
(b) from about 2% to about 40% by weight of at least one polypropylsilsesquioxane film forming resin;
(c) from about 0.5% to about 10% of at least one hydrocarbon-based film forming resin;
(d) from about 15% to about 60% by weight of at least one volatile hydrocarbon solvent;
(e) from about 5% to about 60% of at least one non-volatile silicone oil;
(f) from about 0% to about 15% of at least one polyethylene wax; and
(g) optionally at least one colorant;
wherein the weight percent ratio of the silicone acrylate copolymer (a) to the at least one polypropylsilsesquioxane film forming resin (b) is from about 1:1 to about 4:1 on a dry weight basis; the weight percent ratio of silicone acrylate copolymer (a) plus the at least one polypropylsilsesquioxane film forming resin (b) to the at least one hydrocarbon-based resin (c) is from about 1.5:1 to about 30:1 on a dry weight basis; the total weight percent of the at least one silicone acrylate copolymer (a) plus the at least one polypropylsilsesquioxane film forming resin (b) is greater than about 10% on a dry weight basis; each weight being relative to the total weight of the composition.

In another embodiment the weight percent ratio of the silicone acrylate copolymer (a) to the at least one polypropylsilsesquioxane film forming resin (b) is about 1:1.

In another embodiment the sum of the weight percent of the at least one silicone acrylate copolymer (a) plus the at least one polypropylsilsesquioxane film forming resin (b) is from about 5% to about 60%, or from about 8% to about 55%, or from about 10% to about 50%, or about 11% to about 15%, by weight, relative to the weight of the composition.

The Silicone Acrylate Copolymer (a)

The compositions of the present invention comprise at least one silicone acrylate copolymer.

The at least one silicone acrylate copolymer polymer can be chosen from silicone/(meth)acrylate copolymers, such as those as described in U.S. Pat. Nos. 5,061,481, 5,219,560, 5,262,087 and US 2012/0301415, the entire contents of which are hereby incorporated by reference. They may also be selected from polymers derived from non-polar silicone copolymers comprising repeating units of at least one polar (meth)acrylate unit and vinyl copolymers grafted with at least one non-polar silicone chain. Non-limiting examples of such copolymers are acrylates/dimethicone copolymers such as those commercially available from Shin-Etsu, for example, the products sold under the tradenames KP-545 (cyclopentasiloxane (and) acrylates/dimethicone copolymer), KP-543 (butyl acetate (and) acrylates/dimethicone copolymer), KP-549 (methyl trimethicone (and) acrylates/dimethicone copolymer), KP-550 (tentative INCI name: isododecane (and) acrylate/dimethicone copolymer), and mixtures thereof. Additional examples include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer) and FA 4002 ID SILICONE ACRYLATE (isododecane (and) acrylates/polytrimethylsiloxymethacrylate Copolymer), and mixtures thereof.

Further non-limiting examples include polymers comprising a backbone chosen from vinyl polymers, methacrylic polymers, and acrylic polymers and at least one chain chosen from pendant siloxane groups and pendant fluorochemical groups. Non-limiting examples of such polymers and their synthesis are disclosed, for example, in U.S. Pat. Nos. 4,972,037, 5,061,481, 5,209,924, 5,849,275, and 6,033,650, and WO 93/23446, WO 95/06078 and WO 01/32737, the disclosures of which are hereby incorporated by reference. These polymers may be sourced from various companies. One such company is Minnesota Mining and Manufacturing Company which offers these types of polymers under the tradenames "Silicone Plus" polymers (for example, poly(isobutyl methacrylate-co-methyl FOSEA)-g-poly(dimethylsiloxane), sold under the tradename SA 70-5 IBMMF).

Other non-limiting examples of useful silicone acrylate polymers include silicone/acrylate graft terpolymers, for example, the copolymers described in WO 01/32727 A1, the disclosure of which is hereby incorporated by reference.

According to other embodiments, the polymer comprises a backbone chosen from vinyl backbones, methacrylic backbones, and acrylic polymeric backbones and further comprises at least one pendant siloxane group. Non-limiting examples of such polymers are disclosed in U.S. Pat. Nos. 4,693,935, 4,981,903, and 4,981,902, the disclosures of which are hereby incorporated by reference.

Other useful polymers include those described in U.S. Pat. No. 5,468,477, the disclosure of which is hereby incorporated by reference. A non-limiting example of these polymers is poly(dimethylsiloxane)-g-poly(isobutyl methacrylate), which is commercially available from 3M Company under the tradename VS 70 IBM.

In an embodiment the silicone acrylate copolymer has a glass transition temperature (Tg) above 20° C.

In an embodiment, the silicone acrylate copolymer is an acrylates/dimethicone copolymer having a Tg above 20° C.

The silicone acrylate polymers (a) may be present in the composition of the invention in an amount ranging from about 2% to about 40% by weight, particularly from about 3% to about 33% by weight, more preferably from about 4% to about 30% by weight, and more preferably from about 5% to about 25% by weight, including all ranges and subranges therebetween, relative to the total weight of the composition.

The Polypropylsilsesquioxane Film Forming Resin (b)

The compositions of the present invention comprise at least one polypropyl silsesquioxane film forming resin.

Silsesquioxane resins are a specific form of silicone resin. Silicone resin nomenclature is known in the art as "MDTQ" nomenclature, whereby a silicone resin is described according to the various monomeric siloxane units which make up the polymer. Each letter of "MDTQ" denotes a different type of unit. When the film forming resin is made up predominantly of tri-functional units (or T units), it is generally called a silsesquioxane resin. See, US2006/0292096.

Examples of silsesquioxane resins that may be used in the present invention are alkyl silsesquioxane resins that are silsesquioxane homopolymers and/or copolymers having an average siloxane unit of the general formula $R^1{}_n SiO_{(4-n)/2}$, wherein each R1 is a propyl group, wherein more than 80 mole % of R1 represent a C3-C10 alkyl group, n is a value of from 1.0 to 1.4, and more than 60 mole % of the copolymer comprises $R^1 SiO_{3/2}$ units. As each R1 is a propyl group these polymers are called polypropylsilsesquioxane resins or "t-propyl" silsesquioxane resins. These resins and methods of making them are described, for example in U.S. Pat. No. 8,586,013, 2012/0301415, 2007/0093619, and 2006/0292096, all of which are herein incorporated by reference.

A non-limiting example of a polypropylsilsesquioxane resin suitable for use in the present invention is commercially available from Dow Corning as Dow Corning 670 Fluid or Dow Corning 680 Fluid. These Dow Corning resins have a general formula of $R_n SiO_{(4-n)/2}$ wherein R is independently chosen from a hydrogen atom and a monovalent hydrocarbon group comprising 3 carbon atoms, wherein more than 80 mole % of R are propyl groups, n is a value from 1.0 to 1.4, more than 60 mole % of the copolymer comprises $RSiO_{3/2}$ units, and having a hydroxyl or alkoxy content from 0.2 to 10% by weight, for example between 1 and 4% by weight, preferably between 5 and 10% by weight, and more preferably between 6 and 8% by weight. Preferably, the polypropylsilsesquioxane resin has a molecular weight from about 5000 to about 30,000 and a Tg from about −5° C. to about 5° C.

The film forming polypropylsilsesquioxane resin (b) may be present in the instant compositions in an amount ranging from about 2% to about 40% by weight, preferably from about 4% to about 25% by weight, more preferably from about 5% to about 22% by weight, including all ranges and subranges therebetween, relative to the total weight of the composition.

The Hydrocarbon-based Resin (c)

The compositions of the invention comprise at least one resin chosen from hydrocarbon-based film-forming resins. Such resins are formulated by dissolving them in an appropriate solvent.

The at least one resin chosen from hydrocarbon-based resins of the present disclosure are polyolefins. These polyolefins are generally nonpolar and, at best, only slightly water soluble, if not substantially water insoluble.

In some embodiments, these hydrocarbon-based resins are thermoplastics and often have a low molecular weight. In preferred embodiments, but not in all embodiments, "low molecular weight" means, unless specified otherwise, that the weight average molecular weight of the at least one resin chosen from hydrocarbon-based resins is about 5,000 or less. In another embodiment, the weight average molecular weight is about 2,200 or less. In yet another embodiment, the weight average molecular weight is about 1,000 or less. Of course, a polyolefin that has a slightly higher molecular weight and is a polyolefin that can provide the advantages of the invention is also contemplated by the term "low molecular weight."

The number-average molar masses (Mn) are determined by gel permeation liquid chromatography (THF solvent, calibration curve established with linear polystyrene standards, refractometric detector).

In one embodiment, the at least one resin chosen from hydrocarbon-based resins has a refractive index of less than 1.5 when measured at between 18 and 25 degrees centigrade. In another embodiment, the at least one resin chosen from hydrocarbon-based resins has a refractive index of less than 1.3 when measured at between 18 and 25 degrees centigrade.

The at least one resin chosen from hydrocarbon-based resins includes, without limitation, low molecular weight (MW between approximately 770 and 2200) thermoplastic polyolefins containing C5+olefin, C5+paraffins and/or C5+diolefin monomers. These C5+polyolefins (C5PO) may also be hydrogenated to promote stability. More preferably, these polyolefins are C5-C20 polyolefins, even more preferably, C6-C20 polyolefins, synthesized via thermal or catalytic polymerization of coal-tar fractions, cracked petroleum distillates, terpenes or pure olefinic monomers. Aliphatic feedstreams used to produce these polyolefins are typically composed of C-5 and C-6 paraffins, olefins and diolefins, the main reactive components of which are often piperylenes such as is and trans-1,3-pentadiene. Substituted C-5 and C-6 olefins are often used as feedstreams was well.

C5PO resins may be found in a number of commercial products including, without limitation, those sold by Eastman Chemical Company under the trademark Eastotac® and Piccotac® resins. In one embodiment, the C5PO resin used is a low molecular weight thermoplastic polymer having a refractive index of less than 1.5. In another embodiment, this C5PO resin has a refractive index of less than 1.3. Both Eastotac® and Piccotac® resins can be made from monomers such as trans-1,3-pentadiene, C-15-1,3-pentadiene,2-methyl-2-butene, dicyclopentadiene, cyclo-pentadiene and cyclopentene monomers. Eastotac® resins are usually hydrogenated during manufacture of the resulting resins while the Piccotac® resins are generally not.

Also useful as polyolefins in accordance with the present invention are Piccolyte® polyterpene hydrocarbon resins such as Piccolyte® A115, which is a polymer of alpha-pinene [CAS Reg. No. 31393-98-3] available from Hercules Inc. Resin Division, Hercules Plaza, 1313 North Market Street, Wilmington Del. 19894-0001.

In yet another embodiment, the at least one resin chosen from hydrocarbon-based resins includes, without limitation, low molecular weight, lightly colored, inert thermoplastic resins derived from petrochemical feedstocks. Preferably, these thermoplastic polymers are also partially or fully hydrogenated. Examples of indene resins that may be mentioned include those sold under the reference Escorez 7105 by the company Exxon Chem., Nevchem 100 and Nevex 100 by the company Neville Chem., Norsolene S105 by the company Sartomer, Picco 6100 by the company Hercules and Resinall by the company Resinall Corp. Other examples include certain hydrogenated polycyclopentadienes and hydrogenated styrene/methylstyrene/indene copolymers sold under the trade name Regalite®. Some of the Regalites are made from C 8+monomers which include, without limitation, vinyl toluene, dicyclopentadiene, indene, alpha-methyl styrene, styrene and methyl indene. These low molecular weight hydrocarbon resins may be found in a number of commercial products including without limitation those sold by Eastman Chemical Middelburg BV, Tobias Asserlaan 5, 2517 KC Den Haag, the Netherlands, under the trademarks Regalite®, Eastotac® and Piccotac®. A material that typifies a hydrocarbon resin that may be used in accordance with the present invention is Regalite® R1090 hydrogenated thermoplastic resin. Other useful polyolefins of this type include Regalite® R1125, R1100, R9100, R7100, R81010 and R81100.

Any of the polyolefin materials used herein may further include conventional additives known in the plastics industry. For example, Regalite® R1090 hydrocarbon resin is stabilized with tetrakis [methylene(3,5-di-tert-butyl-4-hydroxyhydrocinnamate)] methane antioxidant.

Other examples of the at least one resin chosen from hydrocarbon-based resins are aliphatic pentanediene resins such as those derived from the majority polymerization of the 1,3-pentanediene (trans or cis-piperylene) monomer and of minor monomers chosen from isoprene, butene, 2-methyl-2-butene, pentene and 1,4-pentanediene, and mixtures thereof. These resins may have a molecular weight ranging from 1000 to 2500. Such 1,3-pentanediene resins are sold, for example, under the references Piccotac 95 by the company Eastman Chemical, Escorez 1304 by the company Exxon Chemicals, Nevtac 100 by the company Neville Chem. or Wingtack 95 by the company Goodyear.

Other examples of the at least one resin chosen from hydrocarbon-based resins include mixed resins of pentanediene and of indene, which are derived from the polymerization of a mixture of pentanediene and indene monomers such as those described above, for instance the resins sold under the reference Escorez 2101 by the company Exxon Chemicals, Nevpene 9500 by the company Neville Chem., Hercotac 1148 by the company Hercules, Norsolene A 100 by the company Sartomer, and Wingtack 86, Wingtack Extra and Wingtack Plus by the company Goodyear.

Other examples of hydrocarbon-based resins are diene resins of cyclopentadiene dimers such as those derived from the polymerization of first monomers chosen from indene and styrene, and of second monomers chosen from cyclopentadiene dimers such as dicyclopentadiene, methyldicyclopentadiene and other pentanediene dimers, and mixtures thereof. These resins generally have a molecular weight ranging from 500 to 800, for instance those sold under the reference Betaprene BR 100 by the company Arizona Chemical Co., Neville LX-685-125 and Neville LX-1000 by the company Neville Chem., Piccodiene 2215 by the company Hercules, Petro-Rez 200 by the company Lawter or Resinall 760 by the company Resinall Corp.

Additional examples of hydrocarbon-based resins are diene resins of isoprene dimers such as terpenic resins derived from the polymerization of at least one monomer chosen from .alpha.-pinene, .beta.-pinene and limonene, and mixtures thereof. These resins may have a molecular weight ranging from 300 to 2000. Such resins are sold, for example, under the names Piccolyte A115 and S125 by the company Hercules, and Zonarez 7100 or Zonatac 105 Lite by the company Arizona Chem.

Mention may also be made of certain modified resins such as hydrogenated resins, for instance those sold under the name. Eastotac C6-C20 Polyolefin by the company Eastman Chemical Co., under the reference Escorez 5300 by the company Exxon Chemicals, or the resins Nevillac Hard or Nevroz sold by the company Neville Chem., the resins Piccofyn A-100, Piccotex 100 or Piccovar AP25 sold by the company Hercules or the resin SP-553 sold by the company Schenectady Chemical Co.

In another embodiment of the invention, the hydrocarbon-based resins used, irrespective of their refractive index, are polyolefins that do not include appreciable amounts (appreciable meaning greater than about 5 percent by weight) of alkylated polyvinyl pyrrolidone monomers, polyvinylpyrrolidone monomers or monoalkyl esters of poly(methylvinylether/maleic acid) as disclosed in U.S. Patent Application Publication No. 2002/0004054(see 0118-0122). In one embodiment, those hydrocarbon-based resins have a refractive index of less than 1.5.

Particular hydrocarbon-based resins useful in the present invention are chosen from indene hydrocarbon-based resins, in particular, the hydrogenated indene/methylstyrene/styrene copolymers sold under the trade name "Regalite®" by the company Eastman Chemical, such as, for example, Regalite® R1100, Regalite® R1090, Regalite® R7100, Regalite® R1010 Hydrocarbon Resin and Regalite® R1125 Hydrocarbon Resin.

Other particular hydrocarbon-based resins useful in the present invention are chosen from thermoplastic polyolefins containing C5+olefin, C5+paraffins and/or C5+diolefin monomers, in particular, C5+polyolefins (C5PO) sold under the tradenames Eastotac® and Piccotac® resins sold by Eastman Chemical Company.

The amount of the at least one resin chosen from hydrocarbon-based resins will depend on a number of factors including, without limitation, the polyolefins or mixture of polyolefins selected, their desired concentration, the solvent or solvent mixture, solubility, the nature of any other components that may be added to the film former or which will interact with the film former once formulated into a cosmetic or personal care composition, the process conditions such as temperature that will be used and the like.

In addition to contributing to improved shine, the hydrocarbon-based resins of the present invention are often characterized by being generally water insoluble and/or offering excellent adherence to the skin. These resins may preferably be formulated by dissolving, dispersing, solubilizing, emulsifying, etc. the hydrocarbon-based resins, such as C5PO, in a hydrocarbon solvent. Particular hydrocarbon solvents useful in formulating the hydrocarbon solvents include, but are not limited to, mineral oils, mineral solvents, mineral spirits, petroleum, petrolatum, waxes, synthetic hydrocarbons, animal oils, vegetable oils, and mixtures of various hydrogen carbons. Water and other aqueous solvents may also be possible for certain formulations in which case a solubilizer or emulsifier may also be desirable. In an embodiment, the at least one resin chosen from hydrocarbon-bases resins is formulated by dissolving a thermoplastic polyolefin in isododecane or a light paraffinic solvent. In another embodiment, the hydrocarbon-based resins may be formulated by dissolving in a non-hydrocarbon solvent such as amyl acetate, butyl acetate, isobutyl acetate, ethyl acetate, propyl acetate or isopropyl acetate.

In the composition of the present invention, the at least one hydrocarbon-based resin (c) is present in an amount of from about 0.5 to about 7.5 percent by weight, or from about 1 to about 6% percent by weight including all ranges and subranges therebetween. In a particular embodiment, the at least one hydrocarbon-based resin (c) is present in an amount from about 2% to about 4% by weight.

The Volatile Hydrocarbon Solvent (d)

The cosmetic compositions of the present invention also contain at least one volatile hydrocarbon solvent Volatile Solvents As used herein "volatile solvent" means any non-aqueous medium capable of evaporating on contact with the skin or the lips in less than one hour at room temperature and atmospheric pressure. "Volatile" solvents typically have a flash point of less than about 100° C.

Non-limiting examples of suitable volatile hydrocarbon solvents include volatile hydrocarbon-based oils having from 8 to 16 carbon atoms, and mixtures thereof, and in particular branched C8 to C16 alkanes such as C8 to C16 isoalkanes (also known as isoparaffins), such as isododecane, isodecane, isohexadecane, which are commercially available under the trade names of Isopar or Permethyl. Also useful are C8 to C16 branched esters, such as isohexyl or isodecyl neopentanoate, as well as alcohols, and mixtures of these compounds. Preferably, the volatile hydrocarbon-based oils have a flash point of at least 40° C.

Examples of volatile hydrocarbon-based oils include, but are not limited to those given in Table 1 below.

TABLE 1

| Compound | Flash Point (° C.) |
|---|---|
| Isododecane | 43 |
| Isohexadecane | 102 |
| Propylene glycol n-butyl ether | 60 |
| Ethyl 3-ethoxypropionate | 58 |
| Propylene glycol methylether acetate | 46 |
| Isopar L (isoparaffin C11-C13) | 62 |
| Isopar H (isoparaffin C11-C12) | 56 |

In an embodiment, the solvent is a volatile solvent selected from isododecane, isooctane, isodecane, isohexadecane, and mixtures thereof.

The at least one volatile hydrocarbon solvent is generally present in the cosmetic composition of the present invention in an amount ranging from about 10% to about 60% by weight, including from about 15% to about 50% by weight, typically from about 17% to about 30% by weight, including all ranges and subranges therebetween, all weights being based on the weight of the composition as a whole.

The Non-volatile Oil (e)

The compositions of the present invention also comprise at least one non-volatile oil. The volatility of the oils can be determined using the evaporation speed as set forth in U.S. Pat. No. 6,338,839, the contents of which are herein incorporated by reference.

These oils include low viscosity oils (having a viscosity from about 5 to about 10 centipoise) and high viscosity oils (having a viscosity of from about 100 to about 10,000 centipoise), and mixtures thereof. In contrast to waxes, oils are liquid at room temperature.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils include wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, *quinoa* oil, olive oil, rye oil, safflower oil, candlenut oil, passion flower oil, musk rose oil and vitamin E oil and the like;

caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7\square 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms; $C_8$ to $C_{26}$ fatty alcohols, for instance oleyl alcohol, cetyl alcohol, stearyl alcohol, and cetearly alcohol; and mixtures of the foregoing oils.

Further, examples of non-volatile oils that may be used in the present invention include, but are not limited to, non-polar oils such as branched and unbranched hydrocarbons paraffin oil, squalane, squalene, mineral oil, pentahydrosqualene, hydrogenated polyisobutene, hydrogenated polydecene, hydrogenated $C_{6-14}$ olefins, polybutene, polydecene, and mixtures of these oils. According to a particular embodiment of the present invention, the oil is a high viscosity oil which is a silicone oil and/or a hydrocarbon oil. "High viscosity" means an oil having a viscosity greater than 100 cSt, particularly greater than 250 cSt at 25° C. Most particularly, the non-volatile oil is selected from a silicone oil.

Such oils are described, for example in US 2011/0293550 and US 2004/0126350, both of which are herein incorporated by reference.

Non-limiting examples of suitable non-volatile silicone oils include polymethylsiloxanes (PDMS) with a linear or cyclic silicone chain, which are liquid or pasty at room temperature, especially cyclopolydimethylsiloxanes (cyclomethicones) such as cyclohexasiloxane; polydimethylsiloxanes (CTFA designation "dimethicones") comprising alkyl, alkoxy or phenyl groups, which are pendent or at the end of a silicone chain, these groups containing from 2 to 24 carbon atoms; polydiethyl siloxanes; phenyl silicones, for instance phenyl trimethicones, trimethyl pentaphenyl trisiloxane, phenyltrimethylsiloxydiphenylsiloxane, trimethylsiloxyphenyl dimethicone, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes; and dimethicone fluids having viscosity values of equal to or greater than 300 cPs; and mixtures thereof.

Specific examples of suitable high viscosity silicone oils include, but are not limited to, Belsil PDM 1000 (1 000 cSt)(trimethylsiloxyphenyl dimethicone) from Wacker and Dow Corning 200 (350 cSt) (the values in parenthesis represent viscosities at 25° C.).

Suitable examples of non-volatile high viscosity hydrocarbon oils include, but are not limited to, fluids having a molecular mass of more than 500 g/mol, for example more than 600 g/mol, and for example more than 650 g/mol. By "hydrocarbon" compound, it is meant a compound comprising principally atoms of carbon and hydrogen and optionally one or more functional groups chosen from hydroxyl, ester, ether and carboxyl functions. These compounds are, according to one aspect, devoid of —Si—O— groups. Suitable examples of hydrocarbon oils include, but are not limited to polybutylenes, such as Indopol H-100 (of molar mass or MM=965 g/mol), Indopol H-300 (MM=1 340 g/mol), and Indopol H-1500 (MM=2 160 g/mol), which are sold or manufactured by Amoco; hydrogenated polyisobutylenes, such as Panalane H-300 E, sold or manufactured by Amoco (M=1 340 g/mol), Viseal 20000 sold or manufactured by Synteal (MM=6 000 g/mol), and Rewopal PIB 1000, sold or manufactured by Witco (MM=1 000 g/mol); polydecenes and hydrogenated polydecenes, such as Puresyn 10 (MM=723 g/mol) and Puresyn 150 (MM=9 200 g/mol) sold or manufactured by Mobil Chemicals; esters such as linear fatty acid esters having a total carbon number ranging from 30 to 70, such as pentaerythrityl tetrapelargonate (MM=697.05 g/mol); hydroxy esters, such as diisostearyl malate (MM=639 g/mol); aromatic esters such as tridecyl trimellitate (MM=757.19 g/mol); esters of C24-C28 branched fatty acids or fatty alcohols, such as those described in EP-A-0 955 039, for example triisocetyl citrate (MM=856 g/mol), pentaerythrityl tetraisononanoate (MM=697.05 g/mol), glyceryl triisostearate (M M=891.51 g/mol), glyceryl 2-tridecyltetradecanoate (MM=1 143.98 g/mol), pentaerythrityl tetraisostearate (MM=1 202.02 g/mol), poly-2-glyceryl tetraisostearate (MM=1 232.04 g/mol) and pentaerythrityl 2-tetradecyltetradecanoate (MM=1 538.66 g/mol); and mixtures of these oils.

Suitable ester oils can also be described according to formula R1COOR2 in which R1 represents a linear or branched higher fatty acid residue containing from 1 to 40 carbon atoms, including from 7 to 19 carbon atoms, and R2 represents a branched hydrocarbon-based chain containing from 1 to 40 carbon atoms, including from 3 to 20 carbon atoms, with R1+R2 ≥10, such as, for example, Purcellin oil (cetostearyl octanoate), isononyl isononanoate, C12 to C15 alkyl benzoate, isopropyl myristate, isopropyl lauroyl sarcosinate, 2-ethylhexyl palmitate, and octanoates, decanoates or ricinoleates of alcohols or of polyalcohols; hydroxylated esters, for instance isostearyl lactate, diisostearyl malate, and ethylhexanoate/stearate/adipate; and pentaerythritol esters. Particular esters include diisostearyl malate, isostearyl hydroxyl stearate, and stearyl heptanoate.

In a particular embodiment the non-volatile oil is a silicone oil, in particular trimethylsiloxyphenyl dimethicone (also known as polyphenyltrimethylsiloxy dimethylsiloxane), such as that available from Wacker under the tradename Belsil PDM 1000.

In an embodiment, the non-volatile oil is selected from stearyl heptanoate, trimethylsiloxyphenyl dimethicone, dimethicone (particularly those with viscosity of 100 cSt and 350 cSt), hydrogenated polyisobutene, and mixtures thereof.

The at least one non-volatile oil is present in the compositions of the present invention in an amount ranging from about 5% to about 60% by weight, including from about 10% to about 50% by weight, typically about 15% to about 40% by weight, more typically from about 20% to about 35% by weight, based on the total weight of the composition, including all ranges and subranges within these ranges.

The Wax (f) (Optional)

The cosmetic compositions of the present invention optionally may contain at least one wax.

For the purposes of the present invention, a wax is a lipophilic fatty compound that is solid at room temperature (25° C.), has a reversible solid/liquid change of state (that is, the state of the material may change based on temperature), has a melting point greater than 45° C., preferably greater than 55° C., more preferably between about 65° C. to about 120° C., and has anisotropic crystal organization in the solid state. The melting point of the wax may be measured using a differential scanning calorimeter (DSC), for example the calorimeter sold under the name DSC 30 by Mettler. For waxes that are derived from petroleum, such as microcrystalline wax, the melting point may be measured according to the drop ASTM method, D-127.

The waxes are those generally used in cosmetics and dermatology. The waxes may be of natural origin, for instance beeswax, carnauba wax, candelilla wax, ouricoury wax, Japan wax, cork fiber wax or sugar cane wax, paraffin wax, lignite wax, microcrystalline waxes, lanolin wax, montan wax, ozokerites and hydrogenated oils, for instance hydrogenated jojoba oil.

The waxes also may be of synthetic origin, for instance polyethylene waxes derived from the polymerization of ethylene, waxes obtained by Fischer-Tropsch synthesis, esters of fatty acids and of glycerides that are solid at 40° C.

Waxes of synthetic origin are preferable as they are more uniform and provide greater reproducibility than waxes of natural origin. Moreover, the waxes are preferably not silicone waxes.

Particular waxes include polyethylene waxes, for example the product sold under the name Performalene 500-L Polyethylene (New Phase Technology), and polymethylene waxes, for instance the product sold under the name Cirebelle 303 (Sasol).

When present in the instant compositions, the at least one wax may be present in an amount ranging from about 10% to about 20% by weight, typically from about 11.5% to 15% by weight, including all ranges and subranges therebetween, all weights based on the weight of the composition as a whole.

Colorant (g)(Optional)

The cosmetic compositions of the present invention optionally may contain at least one cosmetically acceptable colorant such as a pigment or dyestuff.

Non-limiting examples of suitable pigments include, but are not limited to, inorganic pigments, organic pigments, lakes, pearlescent pigments, iridescent or optically variable pigments, and mixtures thereof. A pigment should be understood to mean inorganic or organic, white or colored particles. Said pigments may optionally be surface-treated within the scope of the present invention but are not limited to treatments such as silicones, perfluorinated compounds, lecithin, and amino acids.

Representative examples of inorganic pigments useful in the present invention include those selected from the group consisting of rutile or anatase titanium dioxide, coded in the Color Index under the reference CI 77,891; black, yellow, red and brown iron oxides, coded under references CI 77,499, 77, 492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

Representative examples of organic pigments and lakes useful in the present invention include, but are not limited to, D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 28 Lake (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430) and the dye or lakes based on cochineal carmine (CI 75,570), and mixtures thereof.

Representative examples of pearlescent pigments useful in the present invention include those selected from the group consisting of the white pearlescent pigments such as mica coated with titanium oxide, mica coated with titanium dioxide, bismuth oxychloride, titanium oxychloride, colored pearlescent pigments such as titanium mica with iron oxides, titanium mica with ferric blue, chromium oxide and the like, titanium mica with an organic pigment of the above-mentioned type as well as those based on bismuth oxychloride, and mixtures thereof.

When a colorant is present, the precise amount and type of colorant employed in the compositions of the present invention will depend on the color, intensity and use of the cosmetic composition and, as a result, will be determined by those skilled in the art of cosmetic formulation. However, in an embodiment the compositions include a colorant in an amount of from about 0.5% to about 18%, by weight, more typically from about 3% to about 15% by weight, including all ranges and subranges therebetween, relative to the total weight of the composition.

Additional Optional Additives/Auxiliary Agents

The compositions of the present invention may further comprise any cosmetically or dermatologically acceptable additional additives such as additional thickeners/viscosity increasing agents, additional film formers, plasticizers, antioxidants, essential oils, preserving agents, fragrances, fillers, pasty fatty substances, additional waxes, neutralizing agents, emollients, moisturizers, vitamins, essential fatty acids, sunscreens, surfactants, medicaments, and mixtures thereof. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9$^{th}$ ed. 2002).

In an embodiment the composition of the invention includes a viscosity increasing agent. In a particular embodiment the gelling agent is selected from a modified clay. Non-limiting examples of such gelling agents include hectorite modified with distearyldimethylammonium chloride or modified with stearyldimethylbenzoylammonium chloride. A particular gelling agent is disteardimonium hectorite, which is commercially available, for example, from Elementis under the tradename Bentone Gel (disteardimonium hectorite (and) propylene carbonate).

Other useful gelling agents include silica, such as fumed silica. The fumed silica may have a particle size, which may be nanometric to micrometric, for example ranging from about 5 nm to 200 nm. Particularly useful fumed silicas are those that are finely divided, hydrophilic and having a large number of silanol groups at their surface. Such hydrophilic silicas are available, for example, under the following tradenames, all of which have the INCI name of silica: "Aerosil 130®", "Aerosil 200®", "Aerosil 255®", "Aerosil 300®" and "Aerosil 380®", from the company Degussa, and "CAB-O-SIL HS-5®", "CAB-O-SIL EH-5®", "CAB-O-SIL LM-130®", "CAB-O-SIL MS-55®" and "CAB-O-SIL M-5®" from "Cabot."

A person skilled in the art will take care to select the optional additional additives and/or the amount thereof such that the advantageous properties of the composition according to the invention are not, or are not substantially, adversely affected by the envisaged addition.

These additives may be present in the composition in a proportion from 0% to 99% (such as from 0.01% to 90%) relative to the total weight of the composition and further such as from 0.1% to 50% (if present), including all ranges and subranges therebetween.

The compositions of the present invention are useful as compositions for making up the skin, in particular the lips.

The present invention will be better understood from the examples which follow, all of which are intended for illustrative purposes only.

EXAMPLES

Lipstick compositions in accordance with the present invention as well as comparative and control compositions were prepared as described below. The ingredients employed in each example are provided in Tables 2 and 4.

Preparation of Liquid Lipsticks:

Liquid lipsticks were prepared at varying amounts of the hydrocarbon film former ranging from 0.5% and up to 10% by dry weight. The polymer solutions, wax, non-volatile solvents and a portion of isododecane were blended under high shear at 100° C. until all materials were completely blended. The solution temperature was brought down to 65° C. and Bentone Gel was added under high shear. Once the mixture became homogenous, pigment solution, fragrance and the final amount of isododecane was added to the mixture and blended until homogenous.

TABLE 2

| | Liquid Lipstick Compositions | | | | | | |
|---|---|---|---|---|---|---|---|
| Compound | Ex 1 (Amt %) | Ex 2 (Amt %) | Ex 3 (Amt %) | Ex 4 (Amt %) | Ex 5 (Amt %) | Ex 6 (comparative) (Amt %) | Ex 7 (comparative) (Amt %) |
| acrylates/dimethicone copolymer (40% active)(a) (60% solvent-isododecane) ((KP550) Shin Etsu) | 5.89 8.84 | 5.89 8.84 | 5.89 8.84 | 5.89 8.84 | 5.89 8.84 | 5.89 8.84 | 5.89 8.84 |

TABLE 2-continued

Liquid Lipstick Compositions

| Compound | Ex 1 (Amt %) | Ex 2 (Amt %) | Ex 3 (Amt %) | Ex 4 (Amt %) | Ex 5 (Amt %) | Ex 6 (comparative) (Amt %) | Ex 7 (comparative) (Amt %) |
|---|---|---|---|---|---|---|---|
| poly propylsislesquioxane (72%) (b) (and) isododecane (28%) (Dow Corning 680 Fluid) | 5.65 2.12 | 5.65 2.12 | 5.65 2.12 | 5.65 2.12 | 5.65 2.12 | 5.65 2.12 | 5.65 2.12 |
| Hydrogenated styrene/methyl styrene/indene copolymer(c) (Regalite R11000 CG) | 0.50 | 1.00 | 2.00 | 4.01 | 6.01 | 8.02 | 10.02 |
| disteardimonium hectorite (Benton Gel - Thickener) | 10 | 10 | 10 | 10 | 10 | 10 | 10 |
| isododecane (d) | 10.97 | 10.46 | 9.46 | 7.64 | 5.46 | 3.45 | 1.45 |
| Isohexadecane (d) | 12.69 | 12.69 | 12.69 | 12.69 | 12.69 | 12.69 | 12.69 |
| stearyl heptanoate (e) | 2.67 | 2.67 | 2.67 | 2.67 | 2.67 | 2.67 | 2.67 |
| trimethylsiloxyphenyl dimethicone (e) | 13.36 | 13.36 | 13.36 | 13.36 | 13.36 | 13.36 | 13.36 |
| Dimethicone (viscosity 350 cSt) (e) | 4.12 | 4.12 | 4.12 | 4.12 | 4.12 | 4.12 | 4.12 |
| Hydrogenated polyisobutene (e) | 2.51 | 2.51 | 2.51 | 2.51 | 2.51 | 2.51 | 2.51 |
| Dimethicone (fluid, viscosity 100 cSt) (e) | 8.35 | 8.35 | 8.35 | 8.35 | 8.35 | 8.35 | 8.35 |
| Pigments and Pearls (g) | 9.46 | 9.46 | 9.46 | 9.46 | 9.46 | 9.46 | 9.46 |
| Mica | 2.33 | 2.33 | 2.33 | 2.33 | 2.33 | 2.33 | 2.33 |
| fragrance | 0.39 | 0.39 | 0.39 | 0.39 | 0.39 | 0.39 | 0.39 |
| Ratios (a + b):c | 23.08:1 | 11.54:1 | 5.77:1 | 2.89:1 | 1.92:1 | 1.44:1 | 1.15:1 |
| a + b | 11.54 | 11.54 | 11.54 | 11.54 | 11.54 | 11.54 | 11.54 |

Surface Tack Testing

Sample tackiness of Examples 1-7 was assessed as follows. A thin film of each lipstick composition was placed on a contrast card using the 3 mm draw down bar. The film was allowed to dry over the course of one hour. A texture analyzer was used to quantitatively assess the tack value of the sample. In this test the lower the number, the less tacky the sample. Table 3 below provides the results of this test for the liquid lipstick samples.

TABLE 3

Tack Measurements

| | Ex 1 | Ex 2 | Ex 3 | Ex 4 | Ex 5 | Ex 6 | Ex 7 |
|---|---|---|---|---|---|---|---|
| Tack | 11.06 (±1.01) | 10.16 (±1.00) | 9.76 (±1.17) | 9.42 (±0.88) | 10.44 (±1.9) | 11.44 (±3.25) | 15.32 (±1.06) |

As demonstrated in Table 3 above, comparative Examples 6 and 7 have the highest measured tack value, which is undesirable. It was shown that at concentrations in which the hydrocarbon resin (c) is below 8%, the tack stays relatively consistent and within a desirable range.

Preparation of Solid Lipsticks

Polymer solutions, resin, waxes, non-volatile oils and a portion of isododecane were blended under high shear at 110° C. until all materials were completely blended. The solution temperature was brought down to 65° C. and pigment solution, mica and the final amount of isododecane was added to the mixture and blended until homogenous. Mixtures were poured in a slim lipstick mold and allowed to reach room temperature over the course of 30 minutes. The mold was then chilled on a cooling plate for an addition 20 minutes. Sticks were individually transferred into standard lipstick compartments and allowed to equilibrate at room temperature for 24 hours.

TABLE 4

Solid Lipstick Compositions

| Compound | Ex 8 (Amt %) |
|---|---|
| acrylates/dimethicone copolymer (40% active) (a) (60% solvent-isododecane) (KP550) Shin Etsu | 5.89 8.84 |
| poly propylsislesquioxane (72%) (b) (and) isododecane (28%) | 5.65 2.12 |
| hydrogenated styrene/methyl styrene/indene copolymer (c) (Regalite ® R11000 CG) | 2.00 |
| isododecane (d) | 5.97 |
| Isohexadecane (d) | 12.69 |
| stearyl heptanoate (e) | 2.67 |
| trimethylsiloxyphenyl dimethicone (e) | 13.36 |
| dimethicone (viscosity 350 cSt) (e) | 4.12 |
| hydrogenated polyisobutene (e) | 2.51 |
| red 7 (g) | 1.98 |
| red 28 (g) | 1.12 |
| yellow 5 lake | 0.27 |
| titanium dioxide | 0.76 |
| iron oxides | 0.93 |
| pearls | 4.4 |
| dimethicone (fluid, viscosity 100 cSt) (e) | 8.35 |
| polyethylene (f) | 13.5 |
| mica | 2.33 |
| fragrance | 2.33 |
| (a):(b) | 1.04:1 |
| (a + b):c | 5.77:1 |
| a + b | 11.54 |

The tack of Example 8 and two comparative solid lipstick compositions were measured according to the procedure described above. The results of this test are shown in Table 5 below.

TABLE 5

Tack Measurements

| Sample | Example 8 | Comparative 3 T-propyl/REGALITE | Comparative 4 MQ/Silicone Oil |
|---|---|---|---|
| Tack Value | 3.48 (±2.24) | 12.44 (±2.08) | 21.92 (±5.59) |

In Table 5, Comparative 3 is a solid lipstick comprising polypropylsilsesquioxane resin (T-Propyl) and hydrogenated styrene/methyl styrene/indene copolymer (Regalite®) as the main film formers.

Comparative 4 is a solid lipstick product that incorporates the silicone resin MQ with silicone oils as the plasticizer. This product had the overall highest tack values.

As is shown in Table 5, the composition of Example 8 has a significantly reduced tack relative to commercial solid compositions of Comparative 3 and 4.

Comparative 3, which includes polypropylsilsesquioxane resin and Regalite® has a significantly higher tack value than the inventive composition of Example 8 which also incorporates both of these films formers, but in addition includes a silicone acrylate copolymer. As shown in Table 5, the inclusion of silicone acrylate copolymer in applicants' Example 8 assist in reducing the tack of the lipstick composition.

Example 8 was further tested for perceived comfort and wear using a third party consumer panel which had 59 subjects. The subjects were given a sample of Example 8 and Comparative 4. The subjects applied each respective product for a three day period. Following the application of the first product, the second product was applied for an additional three day period. At the end of the wearing time the subjects were given a questionnaire asking about the sample comfort and wear times. The results of this test are summarized below in Table 6. In terms of comfort, Example 8 was perceived by a greater amount of participants positively in comparison with Comparative 4. Both products had similar overall perceived wear.

TABLE 6

Consumer Study

| Sample | Example 8 | Comparative 4 |
|---|---|---|
| Comfort | 59% | 39% |
| Wear | 53% | 49% |

What is claimed is:

1. A lipstick comprising:
    (a) from about 5% to about 25% by weight of acrylates/dimethicone copolymer having a glass transition temperature greater than 20° C.;
    (b) from about 5% to about 22% by weight of polypropylsilsesquioxane film forming resin having a glass transition temperature of from about −5° C. to about 5° C., wherein the polypropylsilsesquioxane film forming resin (b) has the general formula $R_n SiO_{(4-n)/2}$; wherein R is independently chosen from a hydrogen atom and a monovalent hydrocarbon group comprising 3 carbon atoms, wherein more than 80 mole % of R are propyl groups; n is a value from 1.0 to 1.4; more than 60 mole % of the copolymer comprises $RSiO_{3/2}$ units; said film forming resin (b) having a hydroxyl or alkoxy content from 0.2 to 10% by weight of the resin and a molecular weight from about 5000 to about 30,000;
    (c) from about 1% to about 4% of hydrogenated styrene/methylstyrene/indene;
    (d) from about 10% to about 60% by weight of volatile hydrocarbon solvent selected from the group consisting of isododecane, isooctane, isodecane, isohexadecane, and mixtures thereof;
    (e) from about 10% to about 50% of non-volatile oil;
    (f) wax; and
    (g) colorant;
    wherein the weight percent ratio of the acrylates/dimethicone copolymer (a) to the polypropylsilsesquioxane film forming resin (b) is from about 1:1 to about 4:1 on a dry weight basis; the weight percent ratio of acrylates/dimethicone copolymer (a) plus the polypropylsilsesquioxane film forming resin (b) to the at hydrocarbon-based resin (c) is from about 1.92:1 to about 11.54:1 on a dry weight basis; the total weight percent of the acrylates/dimethicone copolymer (a) plus the polypropylsilsesquioxane film forming resin (b) is greater than about 11% on a dry weight basis; each weight being relative to the total weight of the lipstick.

2. The composition of claim 1, wherein the non-volatile oil (e) is selected from trimethylsiloxyphenyl dimethicone, dimethicone, hydrogenated polyisobutene, stearyl heptanoate, and mixtures thereof.

3. The composition of claim 1, wherein the wax is polyethylene wax.

4. The composition of claim 1, wherein the ratio of the acrylates/dimethicone copolymer (a) to the polypropylsilsesquioxane film forming resin (b) is about 1:1.

5. The composition of claim 1, wherein the weight percent ratio of acrylates/dimethicone copolymer (a) plus the polypropylsilsesquioxane film forming resin (b) to the hydrocarbon-based resin (c) is from about 2.89:1 to about 11.54:1 on a dry weight basis.

6. The lipstick of claim 1, wherein the lipstick is solid.

7. The lipstick of claim 1, wherein the lipstick is liquid.

8. A method of making up lips comprising applying to the lips a lipstick according to claim 1.

* * * * *